(12) United States Patent
Rathbone

(10) Patent No.: US 12,097,090 B2
(45) Date of Patent: Sep. 24, 2024

(54) DRUG DELIVERY DEVICE

(71) Applicant: Michael Rathbone, Hamilton (NZ)

(72) Inventor: Michael Rathbone, Hamilton (NZ)

(73) Assignee: Ulti Pharmaceuticals Limited, Turangi (NZ)

( * ) Notice: Subject to any disclaimer, the term of this patent is extended or adjusted under 35 U.S.C. 154(b) by 102 days.

(21) Appl. No.: 15/742,751

(22) PCT Filed: Jul. 11, 2016

(86) PCT No.: PCT/NZ2016/050113
§ 371 (c)(1),
(2) Date: Jan. 8, 2018

(87) PCT Pub. No.: WO2017/007342
PCT Pub. Date: Jan. 12, 2017

(65) Prior Publication Data
US 2018/0200036 A1   Jul. 19, 2018

(30) Foreign Application Priority Data

Jul. 9, 2015   (NZ) ........................................ 709882

(51) Int. Cl.
*A61D 7/00*     (2006.01)
*A61K 9/00*     (2006.01)
*A61D 19/00*    (2006.01)

(52) U.S. Cl.
CPC .............. *A61D 7/00* (2013.01); *A61K 9/0036* (2013.01); *A61D 19/00* (2013.01)

(58) Field of Classification Search
CPC .. A61D 7/00; A61D 19/00; A61F 6/06; A61F 6/08; A61F 6/14; A61F 6/142; A61F 6/144; A61K 9/0034; A61K 9/0036; A61K 9/0039

USPC .......... 128/833, 839; 424/422–425, 430, 432
See application file for complete search history.

(56) References Cited

U.S. PATENT DOCUMENTS

| | | | | |
|---|---|---|---|---|
| 3,710,795 | A | * | 1/1973 | Higuchi ................... A61D 7/00 424/424 |
| 3,854,476 | A | * | 12/1974 | Dickinson, III .......... A61F 6/08 119/854 |
| 4,155,991 | A | * | 5/1979 | Schopflin .................. A61F 6/08 128/832 |
| 4,292,965 | A | * | 10/1981 | Nash .................... A61K 9/0036 128/833 |

(Continued)

OTHER PUBLICATIONS

Weisman, Abner I, The volumetric capacity of the human nulliparous uterus, Jan. 1951, American Journal of Obstetrics and Gynecology, vol. 61, Issue 1, pp. 202-204 (Year: 1951).*

(Continued)

*Primary Examiner* — Keri J Nelson
(74) *Attorney, Agent, or Firm* — Tracey S. Truitt; Sandberg Phoenix & von Gontard P.C.

(57) ABSTRACT

There are described delivery devices for insertion into a body cavity of a target mammal, the delivery device comprising a resilient frame adapted to receive one or more moulded impregnated masses. The frame, together with the impregnated mass, are insertable, retainable and withdrawable from the intended body cavity. The impregnated mass or masses are attached to the frame to present substantially all of each face of the masses to exposure to a fluid of the body cavity when retained therein.

11 Claims, 5 Drawing Sheets

(56) References Cited

U.S. PATENT DOCUMENTS

| | | | | |
|---|---|---|---|---|
| 4,585,451 | A * | 4/1986 | Millar | A61K 9/0036 |
| | | | | 424/432 |
| 4,678,463 | A * | 7/1987 | Millar | A61M 31/002 |
| | | | | 604/285 |
| 5,398,698 | A * | 3/1995 | Hiller | A61K 9/0036 |
| | | | | 128/830 |
| 6,352,524 | B1 * | 3/2002 | Bunt | A61M 31/002 |
| | | | | 604/285 |
| 6,444,224 | B1 | 9/2002 | Rathbone | |
| 6,663,608 | B2 * | 12/2003 | Rathbone | A61K 9/0036 |
| | | | | 604/286 |
| 2001/0029357 | A1 | 10/2001 | Bunt | |
| 2002/0026158 | A1 * | 2/2002 | Rathbone | A61K 9/0036 |
| | | | | 604/286 |
| 2004/0142012 | A1 | 7/2004 | Bunt | |
| 2010/0168563 | A1 * | 7/2010 | Braver | A61M 31/002 |
| | | | | 600/431 |
| 2010/0215719 | A1 * | 8/2010 | Kohn | A61K 9/0024 |
| | | | | 528/184 |
| 2011/0033519 | A1 * | 2/2011 | Leong | A61K 31/566 |
| | | | | 424/432 |
| 2011/0034901 | A1 * | 2/2011 | Ziv | A61K 9/0036 |
| | | | | 604/285 |
| 2011/0056501 | A1 | 3/2011 | Kortesuo | |
| 2015/0230971 | A1 * | 8/2015 | Wildemeersch | A61F 6/144 |
| | | | | 128/833 |

OTHER PUBLICATIONS

STIC search results for claim limitation search—Mar. 4, 2021 (Year: 2021).*

* cited by examiner

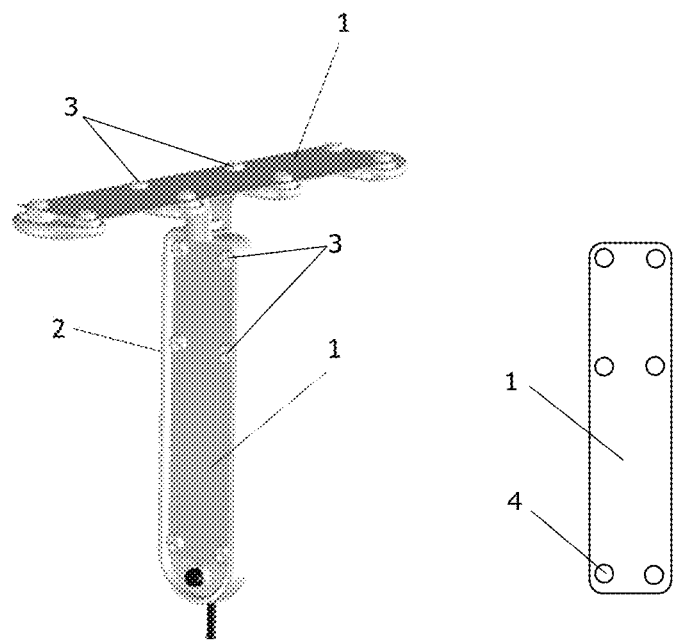
FIGURE 1A
FIGURE 1E
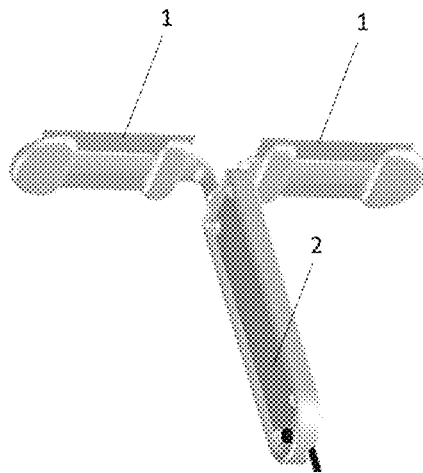
FIGURE 1B

DRUG DELIVERY DEVICE

FIELD OF THE INVENTION

The present invention relates to a drug delivery device for delivering a drug into a body cavity or passage of a mammal, the manufacture of the drug delivery device and its use.

BACKGROUND TO THE INVENTION

Various devices are known for delivering drugs into cavities, such as the vaginal cavity. For example, New Zealand patent 200564 reports an intravaginal device having multiple lobes that form a "Y"-shaped device. The device of NZ 200564 includes the use of silicone rubber or ethylene vinyl acetate (EVA) that has been formed from a heat curable liquid form and which, prior to curing to form the solid form, has a chemical dispersed or dissolved in it. This chemically impregnated solid portion may form the device or be applied as a skin layer onto the device.

New Zealand patent 207341 also reports an intravaginal device formed of a "T"-shaped spine coated in a chemically impregnated material. NZ 207341 reports that the spine is formed from a flexible thermoplastic such as Nylon or polypropylene with the drug carrying coating formed from silicone.

New Zealand patent 230023 additionally reports an intravaginal device formed of a multi-configurable spine impregnated or coated with a drug.

New Zealand patent 286492 additionally reports an intravaginal device formed of a spine covered with a matrix of progesterone containing silicone rubber material formed by injection of the uncured progesterone containing matrix as a liquid into a mold.

PCT patent application published as WO 1998/053758 reports an intravaginal device for pigs that contains a progesterone impregnated matrix about a Nylon spine.

PCT patent application published as WO 1999/040966 (Duirs) reports the use of pods impregnated with a drug, or containing gills or vanes.

PCT patent application published as WO 2002/062415 reports a progesterone impregnated "T" or "Y"-shaped device for insertion into the vagina of a target species.

Cost of manufacture is an important consideration in relation to drug delivery devices. Typically the active agent accounts for a high percentage of the total device cost, followed by the cost of the material (e.g. silicone) used to form the device. Ease of manufacture also significantly contributes to a lower device cost. The devices mentioned above all have disadvantages whether being the amount of active agent residue left within the device after use, or the complexity of manufacture, such as the Duirs device.

It is an object of the present invention to provide a drug delivery device, or to at least provide the public with a useful choice.

SUMMARY OF THE INVENTION

In a first aspect the invention relates to a delivery device for insertion into a body cavity of a target mammal comprising
a resilient frame adapted to receive one or more impregnated masses, the frame together with the impregnated mass being insertable, retainable and withdrawable from the intended body cavity, and
at least one of the impregnated masses being at least substantially laminar and attached to the frame to present substantially all of each face of the masses to exposure to a fluid of the body cavity when retained therein.

In a further aspect the invention relates to a delivery device insertable, retainable and withdrawable from a body cavity of a target mammal, the delivery device comprising
a resilient frame, and
one or more impregnated masses, having a thickness of less than about 0.95 mm, and more preferably about 0.1 to about 0.8 mm, being impregnated with one or more active agents for delivery to the target mammal upon insertion and retention in the target mammal, and
each of the one or more impregnated masses being supported by the resilient frame at, at least two or more separate points of attachment.

In a further embodiment the invention relates to a method of manufacturing a delivery device for insertion into a body cavity of a target mammal comprising
providing a resilient frame,
molding an impregnated mass having a thickness of less than 0.95 mm, and more preferably about 0.1 to about 0.8 mm, and
attaching the molded impregnated mass to the resilient frame such that the molded impregnated mass is supported by the resilient frame on at least two or more separate points of attachment.

In some embodiments the frame is formed from a polymer, natural or synthetic, such as a polycarbonate, a polyethylene, a polypropylene, a Nylon or a combination thereof.

In some embodiments the shape of the frame is in the form of a "T", "t", "Y", "V", "C", "X" or "M"-shape, or wishbone, kite or diamond shaped.

In one embodiment at least one of said impregnated masses is present in or on the frame in a plane and wherein the direction of insertion of said delivery device is parallel to, or in said plane.

In an alternative embodiment at least one of said impregnated masses is present in or on the frame in a plane that is orthogonal to the direction of insertion of said delivery device.

In one embodiment all of the impregnated masses are held in or on the frame in a plane and wherein the direction of insertion of said delivery device is parallel to, or in said plane.

In one embodiment at least one of said impregnated mass or masses are held in or on the frame at an angle relative to the direction of insertion of the delivery device into the animal.

In some embodiments the frame has a deployed and undeployed condition. Preferably when in said deployed condition this retains the delivery device in the body cavity.

In some embodiments the frame includes one or more projections from the main body of the device.

In some embodiments the frame includes lands or bosses on which part of one face that the one or more impregnated masses is held.

In one embodiment the impregnated mass includes openings, scallops or protuberances (3) to engage the frame protuberances, bosses or lands (4).

In some embodiments the frame is in the form of a skeletal frame to support the one or more impregnated masses.

In some embodiments the one or more impregnated masses are at least substantially laminar.

In some embodiments the one or more impregnated masses are planar.

In one embodiment the impregnated masses are formed from a polymer.

In one embodiment the delivery device comprises 2, 3, 4, 5, 6, 7, 8 9, or 10 g of polymer, and useful ranges may be selected between any of these values.

In one embodiment the delivery device comprises 1, 2, 3, 4, 5, 6, 7 or 8 cm$^3$ of polymer, and useful ranges may be selected between any of these values.

In one embodiment the ratio of the surface area of the impregnated mass or masses to the polymer is from 12:1 (surface area:polymer mass) to 60:1 cm$^2$·g$^{-1}$, and useful ranges may be selected between any of these values.

In one embodiment the polymer is selected from a non-degradable thermoset polymer, a non-degradable thermoplastic polymer, a biodegradable polymer or a combination thereof. For example the polymer may be formed from silicone, ethylene vinyl acetate, polycaprolactone, natural (latex) rubber, styrene-butadiene rubber, polyurethane, polyamide (Nylon), low-density polyethylene (LDPE), high-density polyethylene (HDPE), polypropylene, polycarbonate, polyester, polyacrylonitrile, polyolefin, acrylic such as polymethyl methacrylate, polyvinyl chloride, polyvinyl fluoride, polymethacrylate, high impact polystyrene, polystyrene, polysulfone, polybutadiene, polyaryleherketone, polyethylene terephthalate (PET), polyglycolic acid, polylactic acid, polylatic-co-glycolic acid, starches, polybutylene succinate, poly p-dioxane, poly-3-hydroxybutyrate, or a combination thereof.

In one embodiment the one or more impregnated masses contain one or more active agents.

In one embodiment the one or more active agents is distributed throughout the polymer.

In one embodiment the active agent is selected from
a natural or synthetic hormone,
an antibiotic, antifungal or antiviral,
a peptide or protein,
an antiparasitic,
an anti inflammatory,
a mineral,
a vitamin,
trace elements,
growth promotants, and
any combination of (a) to (i) above.

In one embodiment the active agent is a hormone selected from progesterone, estradiol, GnRH, prostaglandins and melatonin.

In one embodiment the active agent is an antibiotic selected from penicillins, cephalosporins, macrolides, fluoroquinolones, sulphonamides, tetracyclines, glycylcyclines, aminoglycosides, carbapenems, or a combination thereof.

In one embodiment the active agent is an anti inflammatory selected from for example non-steroidal anti-inflammatory drugs (NSAIDs), such as for example aspirin, ibuprofen, naproxen, aceclofenac, diclofenac, acetmetacin, dexibuprofen, ketoprofen, dexketoprofen, fenoprofen, flurbiprofen, etodolac, sulindac, indometacin, nebumetone, tiaprofenic acid, meloxicam, selective cyclo-oxygenase-2 (COX-2) inhibitors such as celecoxib, rofecoxib, etoricoxib or a combination thereof.

In one embodiment the one or more impregnated masses have a thickness of less than 0.95, 0.9, 0.85, 0.8, 0.75, 0.7, 0.65, 0.6, 0.55, 0.5 or 0.45 mm, and useful ranges may be selected between any of these values.

In one embodiment the one or more impregnated masses have a thickness of about 0.1, 0.2, 0.3, 0.4, 0.5, 0.6, 0.7 or 0.8 mm, and useful ranges may be selected between any of these values.

In one embodiment the, or each, impregnated mass contain 1, 5, 10, 15, 20, 25, 30, 35, 40 45, 50, 55, 60, 65 or 75% by weight of the active agent, and useful ranges may be selected between any of these values.

In one embodiment, in the case of multiple impregnated masses, each impregnated mass contains a different active agent.

In one embodiment, in the case of multiple impregnated masses, at least two of the impregnated masses contain the same active agent and the same % by weight of that active agent.

In one embodiment, in the case of multiple impregnated masses, at least two of the impregnated masses contain the same active agent, and wherein the said same active agents are present at different % by weight in each of the impregnated masses.

In one embodiment, in the case of multiple impregnated masses, at least two of the impregnated masses have the same thickness.

In one embodiment, in the case of multiple impregnated masses, at least two of the impregnated masses have a different thickness.

In one embodiment the impregnated masses has at least two surfaces of substantially the same surface area, both surface areas being substantially exposed to the fluid of the body cavity upon insertion into the mammal. Preferably at least 70, 75, 80, 85, 90 or 95% of the surface area of both surfaces are exposed to the fluid of the body cavity upon insertion into the mammal.

In some embodiments the delivery device comprises two or more separate impregnated masses, the surface areas (whether exposed or concealed) of the two or more impregnated masses being exposed to the fluid of the body cavity. Preferably at least 70, 75, 80, 85, 90 or 95% of the surface area (whether exposed or concealed) of the two or more impregnated masses are exposed to the fluid of the body cavity upon insertion into the mammal.

In one embodiment the delivery device achieves an active agent release rate of at least about 0.1, 0.15, 0.2, 0.25, 0.3, 0.35, 0.4, 0.45, 0.5, 0.55 or 0.6 mg·cm$^{-2}$·day$^{-1}$, and useful ranges may be selected between any of these values.

In one embodiment each of the one or more impregnated masses are at least generally laminar and have substantially parallel faces.

In one embodiment the impregnated mass includes a release rate modifier. In some embodiments the release rate modifier is selected from inert fillers such as calcium carbonate, salts such as sodium chloride, pore forming substances such as water soluble salts, oils such as *arachis* and liquid paraffin, and surface active agents such as sodium lauryl sulphate.

In one embodiment, the one or more impregnated mass is manufactured by compression molding, extrusion, casting, or injection molding.

In one embodiment the one or more impregnated masses include at least two or more slits, apertures or openings to facilitate attachment to the frame. Preferably such attachment openings are molded into the impregnated masses.

In one embodiment the impregnated masses are moulded in situ with the frame, the frame including two or more slits, apertures or openings. In such an embodiment the silicon of the impregnated mass penetrates the two or more slits, apertures or openings, and upon hardening the penetration secures the impregnated mass to the frame.

In one embodiment the one or more molded impregnated mass are each attached to the frame.

In one embodiment the one or more molded impregnated mass are attached to the frame, yet are spaced from the frame.

In some embodiments the one or more impregnated masses are retained by the frame with or without any seating of any face region of the one or more masses on the frame.

In some embodiments the one or more impregnated masses is held exteriorly over the frame.

In an alternate embodiment the one or more impregnated masses is held within the frame.

In some embodiments the impregnated mass, once attached to the frame, is held in a non-planar orientation.

In alternate embodiments, the impregnated mass, once attached to the frame, is held in a planar orientation.

In one embodiment multiple impregnated masses are attached to the frame.

In one embodiment the one or more masses are spontaneously expressible from the body cavity if detached from the frame.

In some embodiments each of the impregnated masses has a different surface area.

In some embodiments the delivery device is of a shape and size as to be suitable for use with fully grown cattle, heifers, sheep, pigs or camels.

In some embodiments the frame includes a projection to aid withdrawal of the device. In some embodiments the projection is a cord, string or some other flexible material.

In some embodiments, following withdrawal of the delivery device from the mammal, the one or more impregnated masses contain less than 40, 35, 30, 25, 20, 15, 10, 5 or 1% by weight of the original active agent loading, and useful ranges may be selected between any of these values.

In one embodiment at least 70, 75, 80, 85, 90, 95, 96 or 98% of the total notional surface area (i.e. including surface area that may be touching the frame) of the impregnated mass is exposed to a fluid of the body cavity.

In some embodiments the frame provides
an insertable configuration,
a body cavity retainable configuration, and
a withdrawal configuration.

In one embodiment the delivery device is used to control estrous in an animal.

In one embodiment the invention relates to a method of regulating the estrous cycle of an animal comprising inserting the delivery as described into a body cavity of the animal and then after a period of time, withdrawing the device. Preferably the delivery device is inserted into the vaginal cavity of the animal to control estrous, wherein the device releases progesterone upon insertion.

In one embodiment use of the delivery device maintains or achieves a blood plasma progesterone concentration of at least 2 ng/ml.

Reference herein to a "frame" can include both a unitary member (e.g. as molded or cut from an extrusion) or an assembled member. The frame is preferably resilient such that it can be conformed to a condition from which it can relax or at least partly relax if constrained (e.g. as in a body cavity).

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

BRIEF DESCRIPTION OF DRAWINGS

Further aspects of the present invention will become apparent from the following description which is given by way of example only and with reference to the accompanying drawings in which:

FIG. 1A is a side perspective view of a device of the present invention comprising a frame supporting multiple impregnated masses.

FIG. 1B is a bottom perspective view of a device of the present invention comprising a frame supporting multiple impregnated masses.

FIG. 1E is a schematic perspective view of the device of FIG. 1 illustrating the lands.

DETAILED DESCRIPTION OF THE INVENTION

The invention generally relates to a delivery device 3 that is capable of being inserted, retained and withdrawn from a body cavity of a target mammal. The delivery device comprises a resilient frame 2 that supports one or more impregnated masses 1, the impregnated masses 1 having a thickness of less than 0.95 mm, or more preferably about 0.1 to about 0.8 mm, and are impregnated with one or more active agents for delivery to the target mammal upon insertion and retention in the target mammal. Each of the impregnated masses 1 are supported by the resilient frame 2 on at least two or more separate points of attachment.

The delivery device 3 can be inserted into a body cavity of a target mammal and comprises a resilient frame 2 that is adapted to receive one or more impregnated masses 1, the frame 2 together with the impregnated mass 1 being insertable, retainable and withdrawable from the intended body cavity. At least one of the impregnated masses 1 is at least substantially laminar and attaches to the frame to present substantially all of each face of the masses to exposure to a fluid of the body cavity when retained therein.

It should be appreciated that upon use the delivery device 3 delivers the one or more active agent at an efficacious amount or concentration to ensure a desired biological response.

Previous devices require relatively large quantities of silicone and progesterone to be used leading to high residual loading of the active agent in the device after use. In contrast the present device has much lower residual loading after use. For example, the residual active agent loading in the delivery device after use is less than 40, 35, 30, 25, 20, 15, 10, 5% of the original drug loading.

1. Frame

The frame 2 provides the structure upon which the one or more impregnated masses 1 are carried. The frame 2 can be provided in a number of different forms, such as T'", "t", "Y", "V", "C", "X" or "M"-shape, or wishbone, kite or diamond shaped.

The delivery device comprises a frame 2 over or within which the impregnated mass or masses 1 are attached. The delivery device 3 can be configured in a number of ways. In a first embodiment the frame or projections of said frame 2 are arranged on the same plane. In an alternate embodiment the frame 2 comprises multiple projections wherein at least one projection is oriented in a different plane to another projection of said frame 2. For example, one projection of the frame 2 may be arranged in a plane, the plane being parallel or coincident with the direction of insertion of the delivery device into the animal. In an alternate embodiment the projections of the frame 2 may be orthogonal or at some other angle relative to the direction of insertion of the delivery device into the animal.

Figure 1C:
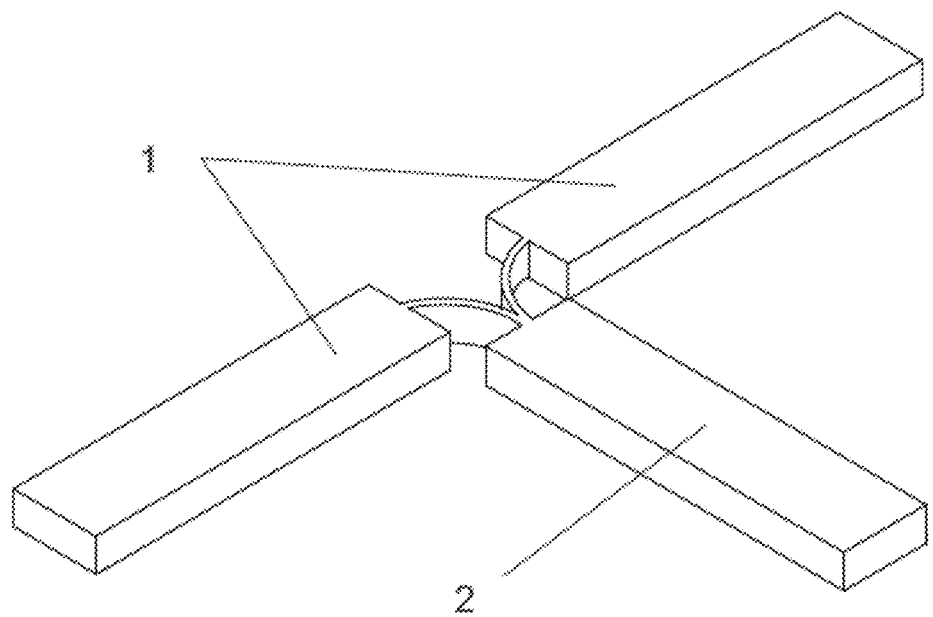
FIG. 1C is a schematic perspective view of an alternative device shown in a deployed condition.
Figure 1D:
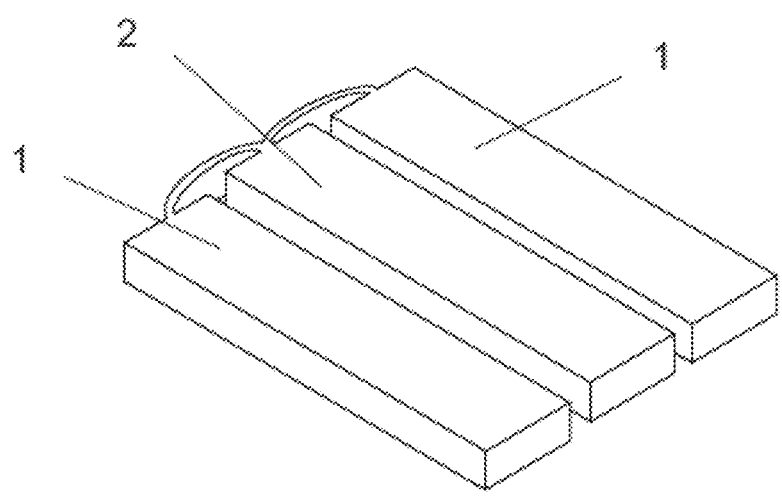
FIG. 1D is a schematic perspective view of the device of FIG. 1C shown in a undeployed condition.

As shown in FIG. 1 is a device in arranged in a "T" shape. The top of the "T" is a projection of the frame 2 wherein it is in a plane (i.e. the insertion direction is "normal" to the plane of the top of the "T") orthogonal to the direction of insertion of the delivery device 3 into the animal. The plane of the stem of the "T" is also parallel to the direction of insertion of the delivery device 3. As shown in FIG. 1 the top of the "T" is in a plane perpendicular to the plane of the stem of the delivery device 3.

In an alternate embodiment the frame 2 (shown in FIG. 1C), is a "T" shape, where the top of the "T" and the stem of the "T" are in the same plane (or at least parallel planes) and the direction of insertion of the delivery device 3 into the animal as parallel. As shown in FIG. 1C the impregnated mass or masses 1 can be attached to the frame 2 such that they are in the same plane as the plane of the frame 2 of the delivery device 3.

The frame 2 can form to a deployed and undeployed condition. The undeployed condition is one in which the frame 2 is restrained to a particular shape. Upon release the frame 2 then forms to the deployed condition. For example, the delivery device 3 is manufactured in the deployed condition and is then forced into the undeployed condition for example through the use of degradable tape, or insertion into a tube. Once delivered into the body cavity of the mammal, the frame 2 deploys to the deployed state owing to its bias to that state.

The frame 2 may be made of any material but is preferably made from plastic. The plastic may be degradable or non-degradable. The plastic may be a thermoplastic. For example, the frame 2 may be formed from a polymer such as a polyethylene, polypropylene, starch-like polysaccharides such as Mater-Bi, polycaprolactone, poly glycolide, poly lactide, polyurethane, rubber, silicone, ethylene vinyl acetate, Nylon, or combinations thereof. Specific examples of suitable polymers include polyamide (Nylon), low-density polyethylene, high-density polyethylene, polypropylene, polycarbonate, polyester, polyacrylonitrile, polyolefin, acrylate such as polymethyl methacrylate), polyvinyl chloride, polyvinyl fluoride, polymethacrylate, high impact polystyrene, polystyrene, polysulfone, polybutadiene, polyaryletherketone, polyethylene terephthalate (PET), polyglycolic acid, polylatic acid, polylactic-co-glycolic acid, polycaprolactone, starches, polybutylene succinate, poly p-dioxanone, poly-3-hydroxybutyrate, or a combination thereof.

The frame 2 may include one or more projections from the main body of the device. For example, the frame may include lands or bosses 4 on which part of one face of the one or more impregnated masses 1 is held. The impregnated mass 1 may include openings, scallops or protuberances to engage the frame 2 protuberances, bosses or lands 4.

The frame 2 can be formed in a variety of shapes, provided it is able to support the one or more impregnated masses 1.

For example, the frame 2 may be formed as a skeletal scaffold to form the basic shape of the device 3. The one or more impregnated masses 1 are then attached to this scaffold.

The frame 2 may act to frame the one or more impregnated masses 1 such that the one or more impregnated masses 1 are held within the confounds of the frame 2. Alternately, the one or more impregnated masses 1 may be placed over the frame 2 and held spaced from the frame 2 by the aforementioned basses bosses or lands 4 as shown in FIGS. 1 and 2.

2. Impregnated Mass

The one or more impregnated masses 1 contain one or more active agents for delivery to a mammal via the body cavity in which the delivery device is located.

One or more impregnated masses 1 is formed from a polymer. The impregnated masses 1 may be formed from a polymer such as a non-degradable thermoset polymer, a non-degradable thermoplastic polymer, a biodegradable polymer or a combination thereof. For example the polymer may be formed from silicone, ethylene vinyl acetate, polycaprolactone, natural (latex) rubber, styrene-butadiene rubber, polyurethane, polyamide (Nylon), low-density polyethylene (LDPE), high-density polyethylene (HDPE), polypropylene, polycarbonate, polyester, polyacrylonitrile, polyolefin, acrylic such as polymethyl methacrylate, polyvinyl chloride, polyvinyl fluoride, polymethacrylate, high impact polystyrene, polystyrene, polysulfone, polybutadiene, polyarylehetherketone, polyethylene terephthalate (PET), polyglycolic acid, polylactic acid, polyclatic-co-glycolic acid, starches, polybutylene succinate, poly p-dioxane, poly-3-hydroxybutyrate, or a combination thereof.

The polymer forms a matrix in which the active agent is retained. Upon delivery and retention in the body cavity the active agent is released from the matrix. The delivery in this manner allows release of the active agent over a period of time, which can be controlled by manipulating the amount, concentration of active agent and the size of the impregnated mass.

The delivery device 3 comprises 2, 3, 4, 5, 6, 7, 8, 9, or 10 g of polymer, and useful ranges may be selected between any of these values (for example, about 2 to about 10, about 2 to about 8, about 2 to about 6, about 3 to about 10, about 3 to about 8, about 3 to about 7, about 4 to about 10, about 4 to about 9, about 4 to about 7, about 5 to about 10, about 5 to about 7, about 6 to about 10, about 6 to about 8 or about 7 to about 10 g). In comparison alternate devices contain higher amount of silicon as shown in Table 1 below.

TABLE 1

The approximate weight of silicone and surface areas to silicone ratio of various intravaginal devices

|  | Weight of silicone per insert (g) | Surface area to silicone weight ratio (cm$^2 \cdot$ g$^{-1}$) |
| --- | --- | --- |
| CIDR 1380 | 13.9 | 8.6 to 1 |
| CIDR 1900 | 19.2 | 6.3 to 1 |
| DIV-B ® | 29.7 | 4.2 to 1 |
| Cronipres TRES USOS | 29.7 | 4.0 to 1 |
| CueMate ® | 12.9 | 10.1 to 1 |
| Device 1 (from examples) | 7 | 17.1 to 1 |
| Device 3 (from examples) | 3 | 40.0 to 1 |

The volume of polymer used in the alternate devices as listed in Table 1 is higher than in the comparable devices of the present invention. In one embodiment the delivery device comprises 1, 2, 3, 4, 5, 6, 7 or 8 cm$^3$ of polymer, and useful ranges may be selected between any of these values, (for example, about 1 to about 8, about 1 to about 6, about 1 to about 5, about 2 to about 8, about 2 to about 7, about 2 to about 5, about 3 to about 8, about 3 to about 7, about 3 to about 6, about 4 to about 8, about 4 to about 6, about 5 to about 8, about 6 to about 8 cm$^3$ of polymer).

The particular design characteristics of the devices of the present invention lead to a high surface area (of the impregnated mass or masses) to polymer ratio. That is, for each unit of polymer, the devices of the present invention have a higher surface area of the impregnated mass or masses compared to other devices, such as those shown above in Table 1. In one embodiment the ratio of the surface area of the impregnated mass or masses to the mas of the polymer of the impregnated mass or masses 1 is from 12:1 (surface area:polymer) to 60:1 cm$^{-1}$, and useful ranges may be selected between any of these values, (for example, about 12:1 to about 60:1, about 12:1 to about 50:1, about 12:1 to about 40:1, about 12:1 to about 30:1, about 12:1 to about 20:1, about 15:1 to about 60:1, about 15:1 to about 50:1, about 15:1 to about 40:1, about 15:1 to about 30:1, about 15:1 to about 20:1, about 25:1 to about 60:1, about 25:1 to about 50:1, about 25:1 to about 40:1, about 25:1 to about 30:1, about 25:1 to about 20:1, about 35:1 to about 60:1, about 35:1 to about 50:1, about 35:1 to about 40:1, about 35:1 to about 30:1, about 35:1 to about 20:1, about 45:1 to about 60:1, about 45:1 to about 50:1, about 45:1 to about 40:1, about 45:1 to about 30:1, about 45:1 to about 20:1 surface area of the impregnated mass or masses to polymer weight).

The one or more impregnated masses 1 are at least substantially laminar. That is, they are molded in a substantially planar form to form a sheet-like form. In some embodiments the one or more impregnated masses may be molded in a non-planar form, but will still retain its sheet-like form. For example, such as a curved sheet.

The one or more impregnated masses 1 has a thickness of about 0.1, 0.2, 0.3, 0.4, 0.5, 0.6, 0.7, 0.8, 0.9 or 0.95 mm, and useful ranges may be selected between any of these values, (for example, about 0.1 to about 0.95, about 0.1 to about 0.9, about 0.1 to about 0.8, about 0.1 to about 0.7, about 0.1 to about 0.5, about 0.1 to about 0.4, about 0.1 to about 0.2, about 0.2 to about 0.95, about 0.2 to about 0.9, about 0.2 to about 0.8, about 0.2 to about 0.6, about 0.2 to about 0.5, about 0.3 to about 0.95, about 0.3 to about 0.9, about 0.3 to about 0.8, about 0.3 to about 0.7, about 0.3 to about 0.5, about 0.4 to about 0.95, about 0.4 to about 0.9, about 0.4 to about 0.8, about 0.4 to about 0.6, about 0.4 to about 0.5, about 0.5 to about 0.8, about 0.5 to about 0.7 or 0.6 to about 0.8 mm)

Each impregnated masses 1 may contain a single active agent or multiple active agents. The one or more active agents are distributed throughout the impregnated mass 1.

Where multiple impregnated masses 1 are attached to a single frame 2, the impregnated masses 1 may all be the same, or there might be a range of impregnated masses with different characteristics, such as different sizes, thicknesses and carrying different active agents.

In this way a delivery device can be customised to deliver a variety of active agents each having their own release profile that suits that active agent.

For example, where there are multiple impregnated masses 1, one mass 1 may have a first thickness, and other masses may have different thicknesses, where thicker or thinner.

Where there are multiple impregnated masses 1, one impregnated masses may contain multiple active agents, and other impregnated masses 1 may contain one active agent, or a combination of different active agents.

The impregnated masses 1 may contain a different concentration of active agents. For example, a first active agent may contain a first concentration of an active agent, and other impregnated masses may contain the same or different active agents at a different (i.e. higher or lower) concentration.

A range of active agents could be utilised. For example the active agent may be selected from a natural or synthetic hormone, an antibiotic, antifungals or antivirals, a peptide or protein, an antiparasitic, an anti inflammatory, minerals, vitamins, trace elements, growth promotants, and any combination thereof.

As specific examples, where the active agent is a hormone, the hormone may be selected from progesterone, estradiol and testosterone.

Where the active agent is an antibiotic, it may be selected penicillins, cephalosporins, macrolides, fluoroquinolones, sulphonamides, tetracyclines, glycylcyclines, aminoglycosides, carbapenems, or a combination thereof. Where the active agent is an anti inflammatory it may be selected from for example non-steroidal anti-inflammatory drugs (NSAIDs), such as aspirin, ibuprofen, naproxen, aceclofenac, diclofenac, acetmetacin, dexibuprofen, ketoprofen, dexketoprofen, fenoprofen, flurbiprofen, etodolac, sulindac, indometacin, nebumetone, tiaprofenic acid, meloxicam, selective cyclo-oxygenase-2 (COX-2) inhibitors such as celecoxib, rofecoxib, etoricoxib or a combination thereof.

In one embodiment the, or each, impregnated mass contain 1, 5, 10, 15, 20, 25, 30, 35, 40 45, 50, 55, 60, 65 or 75% by weight of the active agent, and useful ranges may be selected between any of these values (for example, about 1 to about 75, about 1 to about 60, about 1 to about 50, about 1 to about 40, about 1 to about 30, about 5 to about 75, about 5 to about 70, about 5 to about 65, about 5 to about 55, about 5 to about 40, about 5 to about 20, about 10 to about 75, about 10 to about 60, about 10 to about 50, about 10 to about 40, about 10 to about 30, about 15 to about 75, about 15 to about 65, about 15 to about 55, about 15 to about 25, about 20 to about 75, about 20 to about 60, about 20 to about 40, about 25 to about 75, about 25 to about 65, about 25 to about 60, about 25 to about 35, about 30 to about 75, about 30 to about 60, about 30 to about 40, about 35 to about 75, about 35 to about 65, about 35 to about 40, about 40 to about 75, about 40 to about 60, about 40 to about 50, about 45 to about 75, about 45 to about 60, about 50 to about 75, about 50 to about 70 or about 60 to about 75% by weight of the active agent).

Given the molding of the impregnated mass it contains at least two surfaces of substantially the same surface area, both surface areas being substantially exposed to the fluid of the body cavity upon insertion into the mammal.

In comparison, prior art devices such as those discussed in the background section are formed as a coating of the active agent-impregnated material coated on a spine. In this manner such a device has a single exterior layer and consequently a much lower surface area per volume of active agent impregnated material.

In one embodiment each of the one or more impregnated masses 1 are at least generally laminar and have substantially parallel faces.

In relation to the present device, at least 70, 75, 80, 85, 90 or 95% of the surface area of both surfaces are exposed to the fluid of the body cavity upon insertion into the mammal, and useful ranges may be selected between any of these values (for example, about 70 to about 95, about 70 to about 85, about 70 to about 80, about 75 to about 95, about 75 to about 85, about 80 to about 95, about 80 to about 90, about 85 to about 95 or about 85 to about 90% of the surface area of both surfaces).

In some embodiments the delivery device comprises two or more separate impregnated masses, the surface areas (whether exposed or concealed) of the two or more impregnated masses being exposed to the fluid of the body cavity. Preferably at least 70, 75, 80, 85, 90 or 95% of the surface area (whether exposed or concealed) of the two or more impregnated masses 1 are exposed to the fluid of the body cavity upon insertion into the mammal.

The impregnated mass 1 may also include a release rate modifier that facilitates dissolution or retards diffusion of the active agent from the polymer. Examples of suitable release rate modifiers include inert fillers such as calcium carbonate, salts such as sodium chloride, pore forming substances such as water soluble salts, oils such as *arachis* and liquid paraffin, and surface active agents such as sodium lauryl sulphate.

3. Manufacture

In further preferred embodiments, the substance delivery device 3 may be imbued with an active substance using processing methods such as compression molding, extrusion, casting or injection molding. One advantage of this method is that the manufacturing steps are less than the number required for injection molding of a traditional device as shown in New Zealand patent 207341 discussed above.

The impregnated mass 1 is preferably manufactured using compression, extrusion or injection molding.

Where compression molding is used, the active agent is first mixed with the polymer. For example, 1, 5, 10, 15, 20, 25, 30, 35, 40, 45, 50 or 60% by weight of active agent is fixed with the polymer, and useful ranges may be selected between any of these values (for example, about 1 to about 60, about 1 to about 45, about 1 to about 25, about 1 to about 20, about 5 to about 60, about 5 to about 40, about 5 to about 30, about 5 to about 20, about 5 to about 15, about 10 to about 60, about 10 to about 50, about 10 to about 40, about 10 to about 25, about 10 to about 20, about 15 to about 60, about 15 to about 35, about 15 to about 25, about 20 to about 60, about 20 to about 50, about 20 to about 40, about 25 to about 60, about 25 to about 45, about 25 to about 35, about 30 to about 60, about 30 to about 50, about 30 to about 40, about 35 to about 60, about 35 to about 45, about 40 to about 60, about 40 to about 50, about 45 to about 60, about 45 to about 50 or about 50 to about 60% by weight).

The mixture of active and polymer is then mixed. Preferably the active and polymer are mixed by rollers.

An amount of active/polymer mixture is placed onto the mold cavity. It will be appreciated that the size and shape of the mould cavity is designed to produce the impregnated mass having the desired dimensions.

The active/polymer mixture placed into the mould is heated to about 50, 60, 80, 100, 120, 140, 160, 180, 200, 220, 240, 260, 280 or 300° C., and useful ranges may be selected between any of these values under pressure of about 150, 300, 450, 600, 750, 900, 1050, 1200, 1350, 1500, 1650, 1800, 1950, 2100, 2250, 2400, 2550, 2700, 2850 or 3000 psi until the active/polymer mixture has polymerized and cured into a solidified impregnated mass 1. Once cooled, the impregnated mass can be attached to the frame.

Where extrusion molding is used, the active agent is first mixed with the polymer. For example, 1, 5, 10, 15, 20, 25, 30, 35, 40, 45, 50 or 60% by weight of active agent is fixed with the polymer, and useful ranges may be selected between any of these values (for example, about 1 to about 60, about 1 to about 45, about 1 to about 25, about 1 to about 20, about 5 to about 60, about 5 to about 40, about 5 to about 30, about 5 to about 20, about 5 to about 15, about 10 to about 60, about 10 to about 50, about 10 to about 40, about 10 to about 25, about 10 to about 20, about 15 to about 60, about 15 to about 35, about 15 to about 25, about 20 to about 60, about 20 to about 50, about 20 to about 40, about 25 to about 60, about 25 to about 45, about 25 to about 35, about 30 to about 60, about 30 to about 50, about 30 to about 40, about 35 to about 60, about 35 to about 45, about 40 to about 60, about 40 to about 50, about 45 to about 60, about 45 to about 50 or about 50 to about 60% by weight).

The mixture of active and polymer is then mixed. Preferably the active and polymer are mixed by the use of a bladed stirrer.

The active/polymer mixture is then extruded using an extruder with a die having a cross sectional shape that matches to the cross section of the desired impregnated mass 1.

The extruded impregnated mass 1 may also then be cut into a particular dimension before attachment to the frame 2.

Where injection molding is used, the active agent is first mixed with the polymer. For example, 1, 5, 10, 15, 20, 25, 30, 35, 40, 45, 50 or 60% by weight of active agent is fixed with the polymer, and useful ranges may be selected between any of these values (for example, about 1 to about 60, about 1 to about 45, about 1 to about 25, about 1 to about 20, about 5 to about 60, about 5 to about 40, about 5 to about 30, about 5 to about 20, about 5 to about 15, about 10 to about 60, about 10 to about 50, about 10 to about 40, about 10 to about 25, about 10 to about 20, about 15 to about 60, about 15 to about 35, about 15 to about 25, about 20 to about 60, about 20 to about 50, about 20 to about 40, about 25 to about 60, about 25 to about 45, about 25 to about 35, about 30 to about 60, about 30 to about 50, about 30 to about 40, about 35 to about 60, about 35 to about 45, about 40 to about 60, about 40 to about 50, about 45 to about 60, about 45 to about 50 or about 50 to about 60% by weight).

The mixture of active and polymer is then mixed. Preferably the active and polymer are mixed by the use of a bladed stirrer.

A mold is selected that is of a size and shape such that the inner chamber matches to the desired dimensions of the impregnated mass. The two halves of the mold are clamped together and the active/polymer mixture injected into the mold. The mold is heated to cure the active/polymer mixture into the impregnated mass 1.

Once removed from the mold the impregnated sheet is allowed to cool before attachment to the frame 2.

4. Use

The device of the present invention can be used for administering an active agent to mammals, including domesticated animals such as cattle, heifers, sheep, camels, pigs and goats.

In one embodiment the delivery device 3 is used to control estrous in an animal. The control of estrous typically requires the device to achieve a sufficient blood plasma concentration of progesterone. For example, in bovine animals a blood plasma concentration of at least 2 ng/mL is desired to be maintained to effectively control estrous. In pigs a blood plasma concentration of at least 8-10 ng/mL is desired to control estrous.

One aspect of the invention relates to a method of regulating the estrous cycle of an animal comprising inserting the delivery as described into a body cavity of the animal and then after a period of time, withdrawing the device. Preferably the delivery device 3 is inserted into the vaginal cavity of the animal to control estrous, wherein the device 3 releases progesterone upon insertion.

Benefits of the present invention include at least a cheaper manufacturing process compared to traditional devices such as described in New Zealand patent 200564 and WO 1999/040966, and also more effective use of the active agent given use of the device of the present invention leads to less residual active agent being in the device after use.

For example, an advantage of the present invention is that the one or more impregnated mass 1 exhibits high drug utilization of the substance upon withdrawal from the animal. This means that minimal quantities of the one or more active agent or agents are delivered into the environment.

For example, after use the spent impregnated mass 1 contains less than 40, 35, 30, 25, 23, 21, 19, 17, 15, 13, 11, 9, 7, 5, 3, 1% by weight active agent, and useful ranges may be selected between any of these values (for example, about 1 to about 40, about 1 to about 35, about 1 to about 30, about 1 to about 25, about 1 to about 21, about 1 to about 15, about 1 to about 9, about 3 to about 40, about 3 to about 35, about 3 to about 30, about 3 to about 25, about 3 to about 21, about 3 to about 17, about 3 to about 13, about 3 to about 7, about 5 to about 25, about 5 to about 21, about 5 to about 17, about 5 to about 13, about 5 to about 9, about 7 to about 25, about 7 to about 21, about 7 to about 17, about 7 to about 15, about 7 to about 11, about 9 to about 25, about 9 to about 21, about 9 to about 17, about 9 to about 11, about 11 to about 25, about 11 to about 21, about 11 to about 17, about 11 to about 15, about 13 to about 25, about 13 to about 21, about 13 to about 19, about 15 to about 25, about 15 to about 19, about 17 to about 25, about 17 to about 21, about 19 to about 25, about 19 to about 21, about 21 to about 25% by weight active agent).

Put another way, after use the impregnated mass 1 contains less than 35, 30, 25, 23, 21, 19, 17, 15, 13, 11, 9, 7, 5, 3, 1% of the original amount of active agent, and useful ranges may be selected between any of these values (for example, for example, about 1 to about 25, about 1 to about 21, about 1 to about 15, about 1 to about 9, about 3 to about 25, about 3 to about 21, about 3 to about 17, about 3 to about 13, about 3 to about 7, about 5 to about 25, about 5 to about 21, about 5 to about 17, about 5 to about 13, about 5 to about 9, about 7 to about 25, about 7 to about 21, about 7 to about 17, about 7 to about 15, about 7 to about 11, about 9 to about 25, about 9 to about 21, about 9 to about 17, about 9 to about 11, about 11 to about 25, about 11 to about 21, about 11 to about 17, about 11 to about 15, about 13 to about 25, about 13 to about 21, about 13 to about 19, about 15 to about 25, about 15 to about 19, about 17 to about 25, about 17 to about 21, about 19 to about 25, about 19 to about 21, about 21 to about 25% of the original amount of active agent).

In one embodiment the delivery device 3 achieves an active agent release rate of at least about 0.1, 0.15, 0.2, 0.25, 0.3, 0.35, 0.4, 0.45, 0.5, 0.55 or 0.6 mg·cm$^{-2}$·day$^{-1}$, and useful ranges may be selected between any of these values, (for example, 0.1 to about 0.6, about 0. to about 0.55, about 0.1 to about 0.4, about 0.1 to about 0.3, about 0.15 to about 0.6, about 0.15 to about 0.5, about 0.15 to about 0.4, about 0.2 to about 0.6, about 0.2 to about 0.5, about 0.2 to about 0.4, about 0.2 to about 0.35, about 0.25 to about 0.6, about 0.25 to about 0.55, about 0.25 to about 0.4. 0.3 to about 0.6, about 0.3 to about 0.5, about 0.35 to about 6, about 0.35 to about 0.45, about 0.4 to about 0.6, about 0.4 to about 0.55, about 0.45 to about 0.6 mg·cm$^{-2}$·day$^{-1}$).

A further advantage of the present invention is the ease at which the active release profile can be altered and/or customised in order to optimise the drug delivery device for use in a mammal. Modifying the release of imbued active agent may be achieved, for example, by controlling the surface area of the impregnated mass, the amount of active agent, the concentration of the active agent, the type of polymer use, or a combination thereof.

The substance delivery device 3 may be attached to a plastic shape of proper design that is configured to be an intravaginally administered drug delivery device. The intravaginally administered substance delivery device may be configured to be retained within the vagina of a cow, sheep, camel, pig, deer, goat or any other animal (such as a cat or dog) or human.

The drug delivery device 3 of the present invention may be administered into a range of cavities such as the rumen, rectum or vagina of a mammal.

Examples of body cavities that the invention may be applied to include, but are not limited to, the vagina, rumen of a ruminant animal, stomach of a monogastric animal, colon, rectum, subcutaneous tissue, muscle tissue, urethra, uterus, or eye.

For example, in some embodiments the drug delivery device 3 is an intraruminal delivery device for delivering an active agent to a ruminant such as a cow, sheep, deer or goat. For example, to ensure retention (given the possibility of removal of the device from the rumen during regurgitation), the device 3 may include a retention mechanism. One such example is for the device to have a shape that inhibits removal, such as a "T" or "Y"-shape. The frame 2 of the drug delivery device 3 may provide for an insertable configuration,
a body cavity retainable configuration, and
a withdrawal configuration.

For example, the drug delivery device 3 could have an origination that allows for administration via the oesophagus such that upon delivery the device "opens" up into a retainable form that prevents removal.

In an alternate embodiment the drug delivery device 3 may be an intravaginal device. For example, the shape of the drug delivery device is such to fit easily and comfortably inside an animals vagina. The impregnated mass of the drug delivery device is imbued with sufficient active agent (such as progesterone) to provide exogenous active agent (i.e. the progesterone) sufficient to have a biological effect (e.g. to control the estrous cycle in the case of progesterone). The drug delivery device 3 may also have a cord to facilitate removal after the desired administration period.

The active agent delivered may include natural or synthetic hormones, an antibiotic, antifungals or antivirals, a peptide or protein, an antiparasitic, an anti inflammatory, minerals, vitamins, trace elements, growth promotants, and any combination thereof.

Examples of substances that can be incorporated into the substance delivery device include, but are not limited to, drugs used in estrous control such as natural or synthetic hormones including progesterone, estradiol, GnRH, prostaglandins, melatonin, drugs used to control infections such as antibiotics, antifungals or antivirals, drugs such as proteins and peptides, drugs used to control parasitic infections including anthelmintics such as ivermectin, abermectin, oxfendazole, macrolytic lactones, oxfendazole or levamisole, nutrients such as minerals, vitamins, trace elements, growth promotants.

For intravaginal devices the preferred active agent includes natural or synthetic hormones.

For intraruminal devices the preferred active agent includes antiparasitic such as anthelmintics, anti-bloat, minerals and/or vitamins.

With reference to FIGS. 1A and 1B there is shown a drug delivery device in a "T"-shaped form having multiple impregnated masses 1 located on a frame 2. Such a device could be suitable for intravaginal or intraruminal administration of the drug delivery agent.

Figure 2A:
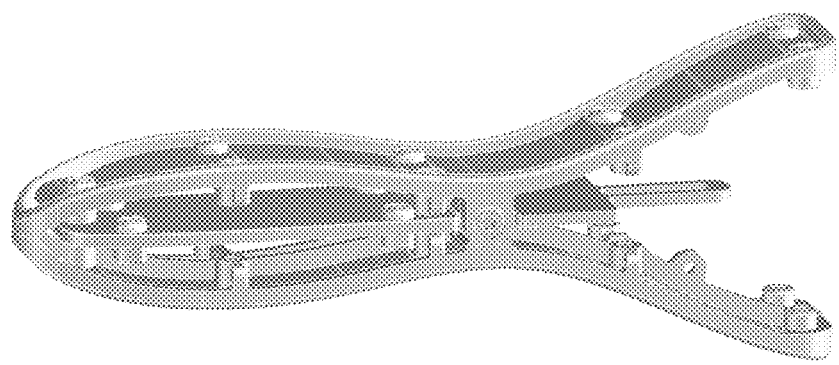
FIGS. 2A and 2B are an alternate design of a device of the present invention.
Figure 2B:
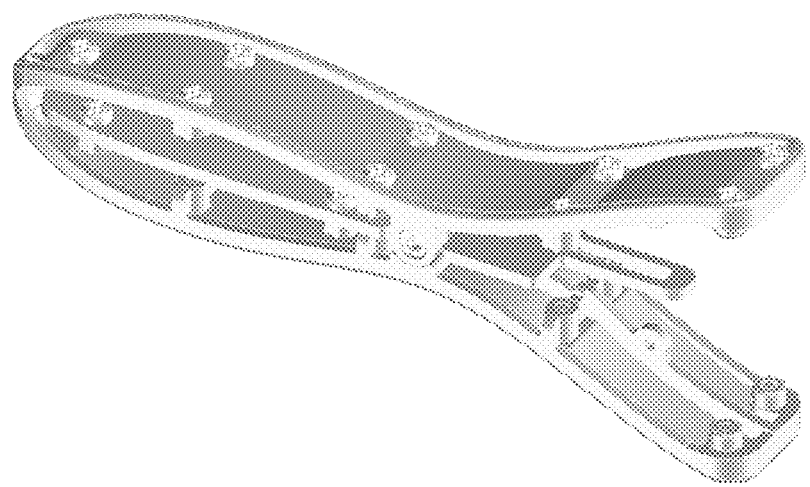

With reference to FIGS. 2A and 2B there is shown a view of a drug delivery device having an alternate design. Such a design may be suitable for intravaginal administration of the drug delivery device. As shown in FIGS. 2A and 2B the device can include multiple impregnated masses, some of which are of a different size. For example, the device of FIGS. 2A and 2B includes three impregnated masses of unequal size: two thin sheets of the invention being of equal size and the remaining sheet of a different size, all imbued with an active agent.

It can be appreciated that different dose amounts of the active substance can be loaded into the substance delivery device thereby providing the opportunity to modify doses delivered into the body cavity of the animal or human. Consequently, the substance delivery device allows for a particular drug delivery profile that is suited to the particular application and needs of the animal.

Drug release from the substance delivery device is influenced by the surface area, thickness of the silicone or drug load. Thus the rate (amount per day), extent (total amount released or drug utilization) and duration (length of treatment) can be predetermined. In addition the substance delivery device may be made with different polymers, with each different polymer being attached to the same plastic shape of proper design, thereby permitting different release rates of different drugs, either simultaneously or sequentially from the same device.

FIGS. 1 and 2 illustrate some possible non-limiting designs that incorporate the substance delivery device attached onto a plastic shape of proper design that is suitable for insertion into a variety of body cavities of animals or humans. It is obvious that different shapes are required for different body cavities, and also that different sizes of the same shape are required for the same body cavity of different species. The different sizes and shapes allow for ease of insertion, ease of removal, comfort, safety and retention of the shape in the different body cavities of different species.

Aspects of the present invention have been described by way of example only and it should be appreciated that modifications and additions may be made thereto without departing from the scope of the patent claims.

EXAMPLE 1—PROGESTERONE DELIVERY DEVICE

The use of a delivery device of the present invention provides the ability to regulate the surface area, thickness and drug load of the substance delivery device allowing the formulator to influence dose levels and to regulate the active agent release profile through a variety of means.

For example, by optimizing progesterone amount, % w/w progesterone load, silicone thickness, and/or surface area, the problems associated with residual progesterone in existing intravaginally administered drug delivery devices containing progesterone for estrous control of fully grown cattle may be reduced or overcome. Improving the progesterone utilization through optimal loading or modification of silicone thickness creates more efficient drug release resulting in a reduced residual. Therefore, release of progesterone in accord with specific dose requirements is achieved while providing minimal residue while meeting specific treatment needs.

A series of experiments were designed to demonstrate that the intravaginal delivery device can be manufactured, inserted into cattle vagina, remain in place for the duration of treatment, be removed from the vagina at the end of treatment, and produce biological effects similar to commercially available intravaginal inserts that are currently on the market.

1. Studies in Intact Animals

This study examines the effect of various delivery device characteristics, such as surface area, the thickness of the impregnated mass, formulation load (% w/w), on plasma progesterone profiles in intact animals.

1.1 Methodology

In this study 24 ovarian intact Brangus beef cattle weighing 300-450 kg received intravaginal delivery devices as shown in Table 2.

FIG. 1 shows the devices used in the in vivo studies. Essentially the devices used in the in vivo trials comprised a nylon spine with a tip-to-tip distance of 14.5 cm and body length of 12.0 cm covered in pads comprising silicone of various thickness (0.3 or 0.5 mm) containing progesterone in % w/w loads of 15.8 or 21% w/w. The surface area of the devices were varied between 115 and 450 $cm^2$, and initial loads ranged between 400 and 2,570 mg. The weight of the silicone impregnated masses ranged from 1,800 to 12,500 mg with volumes varying between 35 and 225 $cm^3$. Impregnated masses were orientated in the same plane to the hinge, but could have equally well been perpendicular to the hinge.

All enrolled cows were subjected to blood sampling prior to insertion of the intravaginal delivery device. From this group 12 cows that exhibited zero progesterone levels at the beginning of the trial were selected for inclusion in the data analysis. Such animals would have their endogenous progesterone suppressed by the exogenous progesterone arising from the intravaginal delivery device, thus the progesterone levels measured in the blood of these cows would only arise from the intravaginal delivery device. Intravaginal delivery devices were administering into the vagina using a plastic applicator. The delivery devices were left in place for seven days before removal.

Animal health, mucous production and retention rate were recorded during the trial. Blood samples were collected in heparinized tubes on a daily basis immediately preceding insertion, each day of the treatment period as well as for three days following removal of the insert. Plasma was separated by centrifugation and stored at −20° C. for subsequent progesterone analysis. Concentrations of progesterone in plasma were determined using a RIA Progesterone Kit (Beckman Coulter). Progesterone plasma concentration versus time (days) were plotted.

insert the less copious was the vaginal secretions. The smallest surface area intravaginal delivery device was observed to produce similar to, or slightly more than, the quantities observed with the commercially available CIDR Cattle inserts. The largest surface area intravaginal delivery devices was observed to produce copious amounts of clear mucous secretions reminiscent of the volumes seen when the previously commercially available PRID coil insert was used.

Figure 3:
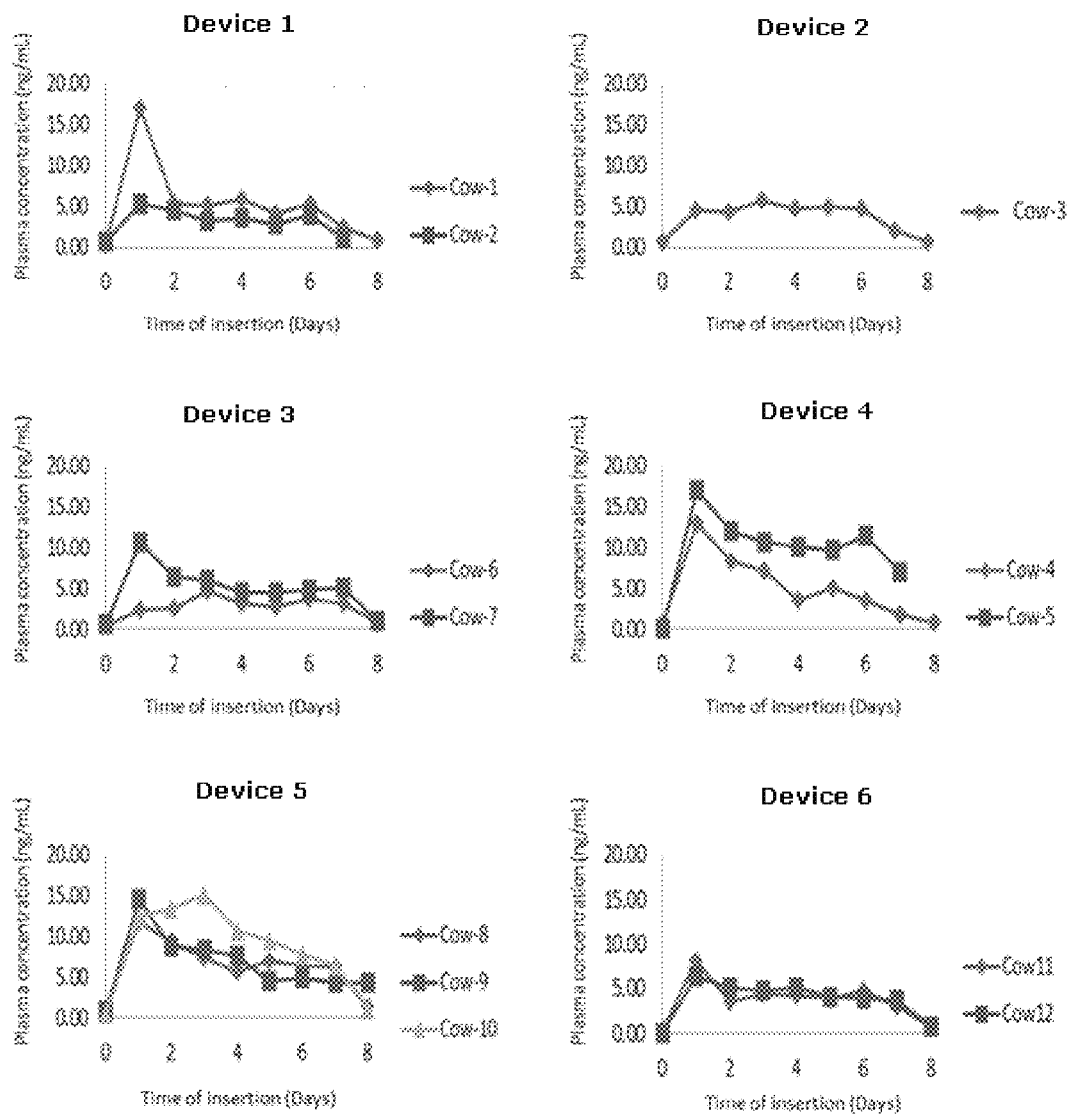
FIG. 3 shows plots of progesterone plasma concentration versus time (days) for each of the different intravaginal delivery devices investigated in the study.

Blood levels in the cows are shown in FIG. 3.

All of the tested intravaginal delivery devices produced a plasma progesterone profile similar to commercially available intravaginal inserts. All of the intravaginal delivery devices produced a rise in progesterone plasma levels which were then sustained until the delivery device was removed. After removal of the intravaginal delivery device plasma progesterone levels fell to basal levels.

Intravaginal delivery devices 1 (115 cm$^2$, 21% w/w, 0.5 mm) and 2 (115 cm$^2$, 21% w/w, 0.3 mm) compared the effect of the impregnated mass thickness on plasma progesterone levels when the impregnated mass surface area (115 cm$^2$) and drug load (21% w/w) were maintained constant. The different thickness impregnated mass intravaginal delivery

TABLE 2

Design of the devices used in the trial.

| | Device 1 | Device 2 | Device 3 | Device 4 | Device 5 | Device 6 |
|---|---|---|---|---|---|---|
| Tip-to-tip wing distance (cm) | 145 | 145 | 145 | 145 | 145 | 145 |
| Length of insert (cm) | 120 | 120 | 120 | 120 | 120 | 120 |
| Frame composition | Nylon | Nylon | Nylon | Nylon | Nylon | Nylon |
| Pad composition | Silicone | Silicone | Silicone | Silicone | Silicone | Silicone |
| Attachment method | Screws | Screws | Screws | Screws | Screws | Screws |
| Pads thickness (mm) | 0.5 | 0.3 | 0.3 | 0.5 | 0.3 | 0.3 |
| Total surface area of pads (cm$^2$) | 115 | 115 | 195 | 450 | 450 | 450 |
| Total weight of silicone (mg) | 3300 | 1800 | 3400 | 12500 | 7200 | 7900 |
| Total volume of silicone (cm$^3$) | 58 | 35 | 59 | 225 | 135 | 135 |
| Active ingredient | Progesterone | Progesterone | Progesterone | Progesterone | Progesterone | Progesterone |
| Initial amount of progesterone (mg) | 660 | 400 | 493 | 2570 | 1530 | 1140 |
| % w/w progesterone | 21 | 21 | 15.8 | 21 | 21 | 15.8 |

Intravaginal delivery devices that were removed on day seven were rinsed in clean water, air dried and stored until residual progesterone contents were determined. Residual progesterone content was determined by using an alcoholic extraction method that involved placing impregnated masses of the intravaginal delivery device into a 250 mL plastic bottle. To this was added 200 mL SDA (denatured ethanol containing 50 ml/L methanol). The bottle was left for greater than 17 hours with occasional shaking by hand until complete extraction of the progesterone. Drug content was quantified by UV at 239 nm after appropriate dilution.

At the end of the study the number of intravaginal delivery devices still remaining in the vagina were recorded. Retention rates were determined from knowledge of the initial number being administered and the number still remaining in the animal vagina at the end the insertion period.

The vaginal reaction to the insert was determined on the day of removal by observing the appearance of mucous production at the end of treatment period.

1.2 Results

All inserts were retained over the seven day insertion period providing a retention rate of 100% in this study. This retention rate is comparable to commercially available intravaginal inserts.

Amounts of mucous observed upon removal varied between intravaginal inserts. The smaller the intravaginal devices showed similar elevations and sustainment of plasma progesterone levels. Intravaginal delivery devices 4 (450 cm$^2$, 21% w/w, 0.5 mm) and 5 (450 cm$^2$, 21% w/w, 0.3 mm) also compared the effect of the thickness of the impregnated mass on plasma progesterone levels when a larger impregnated mass with a surface area (450 cm$^2$) and same drug load (21% w/w) were maintained constant.

Intravaginal delivery device 5 (450 cm$^2$, 21% w/w, 0.3 mm) and 6 (450 cm$^2$, 15.8% w/w, 0.3 mm) compared the effect of the concentration of progesterone (% w/w) in different impregnated masses whose surface area (450 cm$^2$) and thickness (0.3 mm) were maintained constant. The different % w/w intravaginal delivery devices showed similar elevations and sustainment of plasma progesterone levels.

The larger intravaginal delivery devices (devices 4, 5 and 6—450 cm$^2$) showed higher plasma levels compared to the medium sized (device 3—195 cm$^2$) and small sized (device 1 and 2—115 cm$^2$) devices.

This result means that the surface area can be varied, for example, to customise the device for different delivery profiles, such as would be required for use in tropical zone cattle (milk outputs of <25 L) or, for example, in high lactating (>45 L) Holstein cattle.

Table 3 shows the initial progesterone load, % w/w and residual progesterone content in each of the different intravaginal delivery devices investigated in the study after a 7 day insertion period.

TABLE 3

Initial progesterone load and residual progesterone content in each of the different intravaginal delivery devices investigated in the study after a 7 day insertion period

|  | Device 1 | Device 2 | Device 3 | Device 4 | Device 5 | Device 6 |
|---|---|---|---|---|---|---|
| Initial progesterone load before insertion (mg) | 660 | 400 | 493 | 2570 | 1530 | 1140 |
| Amount of progesterone released from the insert over 7 days (mg) | 290 | 310 | 400 | 760 | 610 | 710 |
| Residual progesterone remaining in the insert after 7 days of insertion (mg) | 370 | 90 | 93 | 1810 | 920 | 430 |
| % residual of initial load | 56.1 | 22.5 | 18.9 | 70.4 | 60.1 | 37.7 |
| Amount of progesterone released per day (mg/day) | 41 | 44 | 57 | 109 | 87 | 101 |
| Amount of progesterone released per unit area per day (mg/cm$^2$/day) | 0.36 | 0.39 | 0.29 | 0.24 | 0.19 | 0.23 |

Both the initial progesterone load before insertion, and amount of progesterone released from the insert over 7 days, varied with impregnated mass thickness and surface area. For any given surface area the residual progesterone loads and % residual of initial load were lowest in the thinnest intravaginal inserts. The amount of progesterone released per day was the same for inserts of the same surface area independent of impregnated mass thickness or initial progesterone load. The amount of progesterone released per day increased with increase in surface area of the insert. The amount of progesterone released per unit area per day was similar for all inserts studied.

2. Studies in Intact Animals—In Vivo Drug Release Rate 2.1 Methodology

In this study 72 ovarian intact Brangus beef cattle weighing 300-450 kg received intravaginal delivery devices of various surface areas and skin thickness which were formulated with various % w/w drug loads (see Table 1). The intravaginal delivery device in vivo drug release profile was determined by administering the intravaginal delivery device into the vagina of cattle using a plastic applicator and, after leaving them in place for varying time periods (3, 4, 5, 6 and 7 days), the intravaginal delivery devices were removed (n≥2 per time period). After removal the amount of progesterone remaining in each intravaginal delivery device was determined within each device using an alcoholic extraction method that involved placing the impregnated masses of the intravaginal delivery device into a 250 mL plastic bottle. To this was added 200 mL SDA (denatured ethanol containing 50 ml/L methanol). The bottle was left for greater than 17 hours with occasional shaking by hand until complete extraction of the progesterone. Drug content was quantified by UV at 239 nm after appropriate dilution. Plots of amount progesterone released from the intravaginal delivery device versus time (days) were plotted.

2.2 Results

Throughout the duration of insertion each of the intravaginal delivery devices released more progesterone, in a similar fashion as commercially available intravaginal devices.

Figure 4:
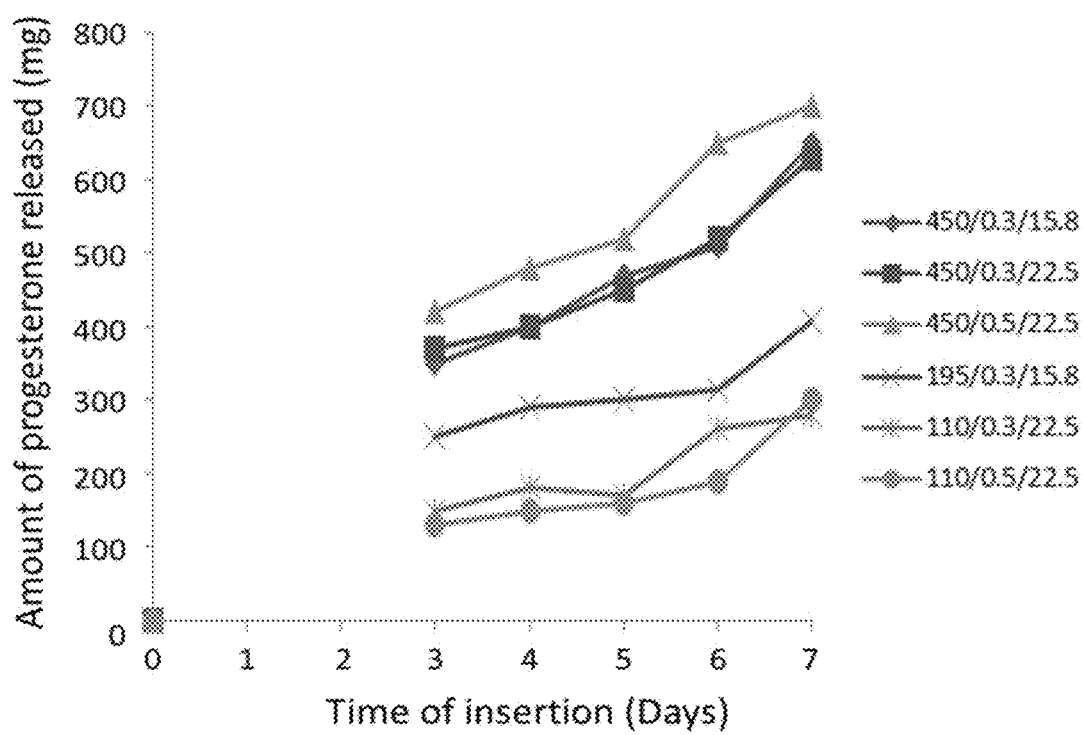
FIG. 4 is a graph of the amount of progesterone released versus time (days) for each of the different intravaginal delivery devices investigated in the study.

FIG. 4 shows a plot of amount of progesterone released versus time (days) for each of the different intravaginal delivery devices investigated in the study.

When comparing intravaginal delivery device 1 (115 cm$^2$, 21% w/w, 0.5 mm) with 2 (115 cm$^2$, 21% w/w, 0.3 mm) and delivery device 4 (450 cm$^2$, 21% w/w, 0.5 mm) with 5 (450 cm$^2$, 21% w/w, 0.3 mm) it can be seen that if the surface area and progesterone concentration (% w/w) are held constant, and only the thickness of the impregnated mass is varied, that similar in vivo progesterone release profiles result.

This result allows for thinner impregnated mass or masses to achieve equivalent progesterone release profiles.

Intravaginal delivery device 3 (195 cm$^2$, 15.8% w/w, 0.3 mm) and 6 (450 cm$^2$, 15.8% w/w, 0.3 mm) show that increasing the surface area of the intravaginal delivery device results in an increase in amount of drug released. This observation is supported when comparing delivery devices 1 (115 cm$^2$, 21% w/w, 0.5 mm) and 4 (450 cm$^2$, 21% w/w, 0.5 mm) and delivery devices 2 (115 cm$^2$, 21% w/w, 0.3 mm) and 5 (450 cm$^2$, 21% w/w, 0.3 mm).

This result means that the surface area can be varied, for example, to customise the device for different delivery profiles, such as would be required for use in tropical zone cattle (milk outputs of <25 L) or, for example, in high lactating (>45 L) Holstein cattle.

Rates of drug release were estimated for each different intravaginal delivery device and are shown in Table 4.

TABLE 4

Rates of drug release for each intravaginal delivery device.

|  | Device 1 | Device 2 | Device 3 | Device 4 | Device 5 | Device 6 |
|---|---|---|---|---|---|---|
| Rates of drug release (mg/cm$^2$/day) | 0.35 | 0.30 | 0.17 | 0.16 | 0.14 | 0.16 |

Table 4 shows that all inserts of the same surface area released drug at the same rate of release regardless of drug load and the thickness of the impregnated mass at each surface area studied because each insert in the study was designed to ensure the % w/w load was above 10% w/w as required. This information can be used to design an intravaginal delivery device with the appropriate release rates leading to the minimal amounts of silicone and progesterone required for the purpose resulting in a low cost-to-manufacture intravaginal insert that delivers sufficient progesterone at the right rate of release over the insertion period to fully control the estrous cycle of cattle.

Table 5 shows the initial progesterone load, % w/w and residual progesterone content in each of the different intravaginal delivery devices investigated in the study after a 7 day insertion period.

TABLE 5

Initial progesterone load and residual progesterone content in each of the different Intravaginal delivery devices investigated in the study after a 7 day insertion period.

| | Device 1 | Device 2 | Device 3 | Device 4 | Device 5 | Device 6 |
|---|---|---|---|---|---|---|
| Initial progesterone load before insertion (mg) | 660 | 400 | 493 | 2570 | 1530 | 1140 |
| Amount of progesterone released from the insert over 7 days (mg) | 300 | 280 | 390 | 700 | 630 | 650 |
| Residual progesterone remaining in the insert after 7 days of insertion (mg) | 360 | 120 | 103 | 1870 | 900 | 490 |
| % residual of initial load | 54.5 | 30.0 | 20.9 | 72.8 | 58.8 | 43.0 |
| Amount of progesterone released per day (mg/day) | 43 | 40 | 56 | 100 | 90 | 93 |
| Amount of progesterone released per unit area per day (mg/cm$^2$/day) | 0.37 | 0.35 | 0.29 | 0.22 | 0.20 | 0.21 |

The initial progesterone load before insertion and amount of progesterone released from the insert over 7 days varied with impregnated mass thickness and surface area. For any given surface area the residual progesterone loads and % residual of initial load were lowest in the thinnest intravaginal delivery devices. The amount of progesterone released per day was the same for intravaginal delivery devices of the same surface area independent of impregnated mass thickness or initial progesterone load. The amount of progesterone released per day increased with increase in surface area of the insert. The amount of progesterone released per unit area per day was similar for all intravaginal delivery devices studied.

The residual observations highlight an advantage of the intravaginal delivery devices over commercially available inserts. The use of thinner impregnated masses (0.3 mm) results in the residual amount of progesterone remaining in a intravaginal delivery device to be lower (less than 90 mg) compared to commercially available inserts (for example the CIDR 1900 cattle insert and CIDR 1380 cattle inserts that exhibit a residual progesterone content after 7 days of inserts of 1250 mg and 730 mg, respectively).

EXAMPLE 3—MANUFACTURE OF FLAT SHEETS USING EXTRUSION MOLDING

Progesterone (21% by weight) is accurately weighed and added to a sufficient quantity of accurately weighed silicone material and homogenously mixed by a bladed stirrer.

The silicone/progesterone mixture is delivered to a barrel. The plastic is then forced through an orifice in a custom steel die with a shape of the cross section of the intended part, forming a flat sheet continuous workpiece.

The workpiece is cooled and then cut into the desired shape by using predefined shaped cutters before attaching onto a preformed spine manufactured by injection molding.

EXAMPLE 4—MANUFACTURE OF FLAT SHEETS USING INJECTION MOLDING

Progesterone (21% by weight) is accurately weighed and added to a sufficient quantity of accurately weighed silicone material and homogenously mixed by a bladed stirrer.

The two halves of the mold are securely closed and the hydraulically powered clamping unit exerts sufficient force to keep the mold securely closed while the material is injected.

Next the mixture is fed into the injection molding machine, and advanced towards the mold by the injection unit. An accurately metered amount of silicone/progesterone mixture is then injected into the mold (shot). The silicone that is inside the mold is then heated in order to cure it.

After sufficient time has passed, the heated silicone/progesterone flat sheet is removed from the mold. Once the part has been ejected, the mold is clamped shut for the next shot to be injected.

The cured silicone/progesterone flat sheet part is then allowed to cool. The cooled cured flat sheets are then attached onto a preformed spine manufactured by injection molding.

I claim:

1. A delivery device insertable, retainable and withdrawable from a body cavity of a target non-human mammal, the delivery device comprising
    a resilient frame, and
    one or more impregnated masses having a sheet-like form to define substantially parallel faces and formed from a polymer, having a total thickness of about 0.1 mm to about 0.95 mm, being impregnated with one or more active agents for delivery to the target non-human mammal upon insertion and retention in the target non-human mammal, and
    each of the one or more impregnated masses
        being supported by the resilient frame on at least two or more separate points of attachment, the remainder of the one or more impregnated masses being spaced from the frame,
        being adapted to expose their faces to the body cavity, and
        having a ratio of the exposed surface area of the one or more impregnated mass or masses to the mass of the polymer of the one or more impregnated masses from 12:1 cm$^2 \cdot$g$^{-1}$ to 60:1 cm$^2 \cdot$g$^{-1}$.

2. A delivery device of claim 1 wherein the one or more impregnated masses are substantially laminar to thereby comprise two opposed faces.

3. A delivery device of claim 2 wherein the resilient frame presents substantially all of each face of the one or more impregnated mass or masses to exposure to a fluid of the body cavity when retained therein.

4. A delivery device of claim 1 wherein the resilient frame includes one or more projections, from which the one or more impregnated masses is held to the resilient frame.

5. A delivery device of claim 4 wherein the one or more impregnated masses includes openings, scallops or protuberances to engage protuberances, bosses or lands of the resilient frame.

6. A delivery device of claim 1 wherein the one or more impregnated masses are formed from a polymer, and the delivery device comprises about 2 g to about 10 g of polymer.

7. A delivery device of claim 6 wherein the delivery device comprises about 1 cm$^3$ to about 8 cm$^3$ of polymer.

8. A delivery device of claim 1 wherein the, or each, of the one or more impregnated masses contains about 1% to about 75% by weight of the one or more active agents.

9. A delivery device of claim 1 wherein each of the one or more impregnated masses have at least two surfaces of substantially the same surface area, the surface areas of the at least two surfaces being substantially exposed to the fluid of the body cavity upon insertion into the target non-human mammal.

10. A delivery device of claim 9 wherein at least 70% to about 95% of the surface area of the at least two surfaces are exposed to the fluid of the body cavity upon insertion into the target non-human mammal.

11. A delivery device of claim 1, wherein a ratio of the exposed surface area of the one or more impregnated mass or masses to the mass of the polymer of the one or more impregnated masses is from 15:1 $cm^2 \cdot g^{-1}$ to 60:1 $cm^2 \cdot g^{-1}$.

\* \* \* \* \*